(12) United States Patent
Ascheman et al.

(10) Patent No.: US 6,354,138 B1
(45) Date of Patent: Mar. 12, 2002

(54) VALIDATION PROCESS FOR PERMEATION MEASUREMENTS THROUGH CLOSED CONTAINERS

(75) Inventors: Timothy A. Ascheman, Ramsey; Michelle Stevens, Minneapolis, both of MN (US)

(73) Assignee: Mocon, Inc., Minneapolis, MN (US)

( * ) Notice: Subject to any disclaimer, the term of this patent is extended or adjusted under 35 U.S.C. 154(b) by 0 days.

(21) Appl. No.: 09/511,597

(22) Filed: Feb. 23, 2000

(51) Int. Cl.[7] .............................................. G01N 15/08
(52) U.S. Cl. ............................. 73/38; 73/49.8; 73/49.3; 73/1.06
(58) Field of Search ............................. 73/38, 40, 49.3, 73/49.8, 64.47, 1.06

(56) References Cited

U.S. PATENT DOCUMENTS

| | | | | |
|---|---|---|---|---|
| 3,466,925 A | * | 9/1969 | Ziegenhagen et al. | 73/38 |
| 3,498,110 A | * | 3/1970 | Brun | 73/38 |
| 3,561,254 A | * | 2/1971 | Argund et al. | 73/38 |
| 3,636,751 A | * | 1/1972 | Pasini, III et al. | 73/38 |
| 4,555,934 A | * | 12/1985 | Freeman et al. | 73/38 |
| 4,561,289 A | * | 12/1985 | Jones | 73/38 |
| 4,622,643 A | * | 11/1986 | Dotson | 364/556 |
| 4,627,270 A | * | 12/1986 | Jones | 73/38 |
| 4,671,100 A | * | 6/1987 | Doussiet | 73/38 |
| 4,715,212 A | * | 12/1987 | Johanson | 73/38 |
| 4,750,918 A | * | 6/1988 | Sirkar | 55/16 |

* cited by examiner

*Primary Examiner*—Hezron Williams
*Assistant Examiner*—David J. Wiggins
(74) *Attorney, Agent, or Firm*—Paul L. Sjoquist

(57) ABSTRACT

A method for validating permeation measurements through closed containers including closure members, by making a first measurement of permeation through a container of a first size, and making a second measurement of permeation through a container of a second size, both with the same closure members, and subtracting the permeation measurement contributions respectively made by the closure members.

5 Claims, 1 Drawing Sheet

VALIDATION PROCESS FOR PERMEATION MEASUREMENTS THROUGH CLOSED CONTAINERS

BACKGROUND OF THE INVENTION

This invention relates to a process for validating permeation measurements made through closed containers; more particularly, the process is useful in validating permeation measurements through materials forming closed containers, where the containers have one or more closure members which may contribute to leakage and may therefore be a source of error in the permeation measurements.

The permeation of organic and other vapors through the walls of a closed container can be measured according to techniques which are well known in the prior art. For example, the closed container can be filled or partially filled with the liquid whose vapor permeation is of interest, and the container can be placed within a chamber through which an inert carrier gas such as nitrogen is permitted to flow. The inert carrier gas will pick up vapor molecules which have permeated through the walls of the container as the carrier gas flows through the chamber, and the carrier gas is subsequently passed through a vapor detector where a measurement may be made of the vapor gas concentration contained in the carrier gas. This measurement can be normalized to provide a calculation of the amount of vapor permeating through the container walls per square meter per day, to provide a basis for comparing the relative permeation through a number of different materials which undergo the same tests, and therefore to provide a basis for selecting materials which permit the least permeation in actual practice.

Since the permeation measurements described above frequently involve very small measured quantities, frequently in the range of parts per billion, it becomes extremely important to prevent any spurious leakage anywhere in the testing apparatus or, to be able to quantify any leakage that may exist in the testing apparatus or in the materials being tested. When the closed container undergoing testing contains closures of one type or another, the leakage through the closures becomes a significant factor which must be accounted for. Even a tiny amount of leakage through a supposed "sealed" closure can distort the measurements sufficiently to render the test results unreliable or meaningless, and therefore a closure "seal" on a container demands particular attention, either to ensure that the closure is completely sealed or to account for the amount of vapor leakage through the closure. However, when permeation measurements involve vapor permeation in the parts per billion range, it is virtually impossible to know for certain whether the container closure is contributing to or distorting the measurements. It is therefore very important to be able to account for any leakage which may exist through closures, and the present invention provides a process for accounting for such leakage, and thereby validating the permeation measurements made through any of the well known techniques which are used in practice.

The invention is particularly adaptable for validating permeation measurements made through tubular materials such as hoses or other liquid flow lines, but it can also be used for evaluating heat seals on plastic containers or closure members on a variety of containers.

SUMMARY OF THE INVENTION

A process for validating permeation measurements through closed containers containing one or more closure members, comprising the steps of making a first permeation measurement through a container of a predetermined first size with the closure member(s) in place, and next making a second permeation measurement through a container of the same material and thickness, of a predetermined second size with the closure member(s) in place, and then calculating the theoretical permeation difference or ratio of the two sizes of material and subtracting an equal permeation measurement contribution from the first and second permeation measurements until the actual permeation difference or ratio of the two permeation measurements is in the same relative relationship as the theoretical difference or ratio.

DESCRIPTION OF THE PREFERRED EMBODIMENT

Figure 1:
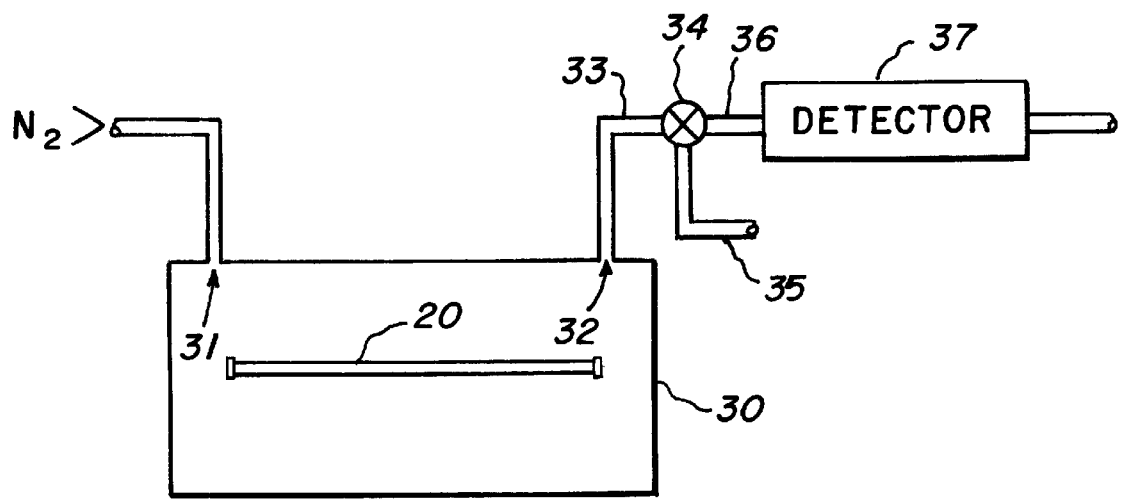
FIG. 1 shows a schematic view of a typical test setup for measurement of the permeation of vapors through a closed container.

Referring first to FIG. 1, there is shown a schematic diagram of a typical test setup for measurement of the permeation of vapors through a closed container. For purposes of example, the diagram illustrates a length of tubing 20 contained within a closed chamber 30; the chamber 30 is completely closed except for an inlet 31 and an outlet 32, intended for permitting the passage of gas into and out of the chamber 30. The inlet 31 is connected to a source of carrier gas, preferably nitrogen ($N_2$), or some other inert gas. The outlet 32 is connected to an outlet conduit 33 which is connected to a valve 34. Valve 34 has one outlet 35 exhausting to atmosphere and a second outlet 36 connected to a suitable detector 37. The choice of detector used as detector 37 depends on the type and nature of the vapors which are intended for analysis. For example, if the vapors permeating through the walls of the test tubing 20 include oxygen, then the detector 37 will be selected from the group of detectors capable of detecting oxygen; if the vapors which are to be measured are organic in nature, the detector 37 could be a flame ionization detector coupled to a gas chromatograph, or similar device. In any event, the type and nature of detector required is dependent on the type and nature of vapors being measured, and the selection of detector is well within the skill of those familiar with technology relating to vapor detection. For purposes of the example used to describe this preferred embodiment, it will be presumed that the tubing 20 is a gasoline delivery hose of the type used in internal combustion engines, and the desired test is to measure the permeation of gasoline vapors through the walls of tubing 20.

Figure 2:
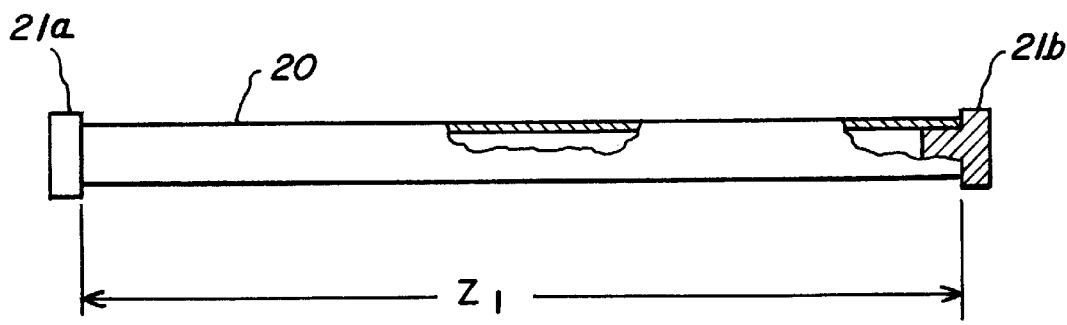
FIG. 2 shows a diagram of the measurement parameters of a first length of closed tubing.

The length of tubing 20 is further illustrated in FIG. 2; tubing 20 has a predetermined length $Z_1$, which may be any convenient length suitable for containment within chamber 30. The tubing 20 has a closure member 21a and 21b at its respective ends to provide a seal to enclose a liquid, gasoline in this example, within the interior of tubing 20. In the example shown, the closure members 21a and 21b are plugs sized to snugly fit inside the walls of tubing 20, to provide a seal against leakage of vapors from the tubing ends, between the tubing walls and the closure member, However, it is known that, for any practical closure member, there will always be some minute leakage of vapor through the tubing ends, and the present invention is intended to account for this leakage in order to provide an accurate measurement of the vapor permeation through the tubing walls, notwithstanding some undesirable vapor leakage through the tubing end closures.

Using the test setup illustrated in FIG. 1, it is possible to measure the amount of gasoline vapor permeation through the walls and ends of tubing 20, which we will define as $P_r$. We will further define the amount of permeation of vapors through-both ends of tubing 20, including the closure members shown in FIG. 2, as $a_p$, and the permeation of vapors through the walls of the tubing length $Z_1$ as an amount $x_{p1}$, which leads to the equation:

$$P_{r1} = a_p + x_{p1} \quad \text{(Equation 1);}$$

where $P_{r1}$ is the total measured permeation through a length of tubing $Z_1$, including permeation through the tubing walls and permeation (leakage) through the closure members.

For any length of tubing $Z_2 = m(Z_1)$, assuming identical closure members 21a and 21b, the total permeation can be expressed as:

$$P_{r2} = a_p + m(x_{p1}) \quad \text{(Equation 2);}$$

where "m" is any integer or fractional number.

Figure 3:
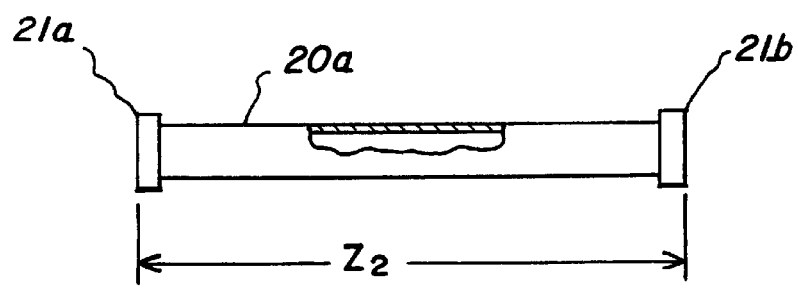
FIG. 3 shows a diagram of the measurement parameters of a second length of closed tubing.

FIG. 3 illustrates a further length of tubing 20a, with the same closures 21a and 21b. It is presumed that tubing 20a is the identical type of tubing as 20, and may in fact be simply a shorter section of the same tubing 20, where the value "m" can be measured as a function of the original length of tubing 20. From Equation 1 we solve for $x_{p1}$:

$$x_{p1} = P_{r1} - a_p \quad \text{(Equation 3);}$$

substituting this value into Equation 2:

$$P_{r2} = a_p + m(P_{r1} - a_p) \quad \text{(Equation 4);}$$

Here we can make a first measurement validation, by first testing the tubing length $Z_2$ of FIG. 3 to obtain the measured total permeation $P_{r2}$, and then comparing this measured value against the measured total permeation $P_{r1}$ of the tubing length of FIG. 2 by taking the ratio $P_{r2}/P_{r1}$ to determine if the ratio is equal to "m". If it is equal, or very nearly equal to "m", then it can be presumed that the amount of leakage through the closure members 21a and 21b is negligible, or at least very much less than the permeation through the walls of the tubing. We can further presume that the two permeation measurements are each accurate, leading to permeation measurements that differ only by the factor "m", which is the result we would expect from measurements of two different lengths of the same tubing.

If the foregoing ratio $P_{r2}/P_{r1}$, does not equal "m", or very closely thereto, we can presume that either one or both measurements are inaccurate or there is a significant leakage through the closure members 21a and 21b. To make this determination we must use Equation 4 to solve for the leakage value $a_p$:

$$a_p = (P_{r2} - mP_{r1})/(1-m) \quad \text{Equation 5;}$$

it is then necessary to run a third test using a different tubing length $Z_3$ to obtain a third permeation measurement $P_{r3}$, and then to solve for the permeation through this third tubing length:

$$X_{p3} = P_{r3} - a_p \quad \text{Equation 6;}$$

and then to compare this third tubing permeation calculation against calculations from the first and second tubing lengths, to verify that the calculated $x_{pn}$'s differ only from one another by the difference in respective tubing lengths.

The foregoing teachings can also be used to calculate closure leakage amounts, to evaluate the relative leakages through a number of different closure members, each applied to the same length of tubing and tested as described above. Likewise, the method can be used to evaluate different fittings for tubing and hoses by similar steps, and various means for attaching fittings and closures to tubing and hoses.

The foregoing teachings can be extended to perform similar tests on heat-sealed pouches and bags, and to evaluate various forms and types of heat seals and other closures for bags and pouches.

The present invention may be embodied in other forms without departing from the spirit or essential attributes thereof; and it is, therefore, desired that the present embodiment be considered in all respects as illustrative and not restrictive, reference being made to the appended claims rather than to the foregoing description to indicate the scope of the invention.

What is claimed is:

1. A method of validating permeation measurements of vapors, made through closed containers containing one or more closure members, by subtracting the contribution to permeation measurement caused by the one or more closure members, comprising the steps of:

a) measuring the permeation of vapors through a first container of a first predetermined size, with the one or more closure members in place;

b) varying the surface area size of the first container by a predetermined factor "m", to form a second closed container of the same material as the first closed container, thereby forming a second closed container having a surface area of "m" times the surface area of said first container, with the one or more closure members in place on the second closed container;

c) measuring the permeation of vapors through the second container;

d) reducing the measured permeation values of both the first container and the second container by equal increments until the respective reduced measurement values are in the same ratio as the factor "m"; and e) using the reduced measurement permeation values as respective measurements of the actual permeation through the first and second containers, thereby correcting for the contribution of the closure members to the measured permeation values and thereby validating the permeation measurements.

2. The method of claim 1, wherein the first closed container is a tubular member of length $Z_1$ having closure members at respective ends; and the second closed container is a tubular member of the same material as the first closed container, of length $Z_2$, wherein $Z_2 = mZ_1$, having the same closure members at respective ends; and wherein the respective measured permeation values of the first closed container and the second closed container are reduced by equal amounts until the ratio of the reduced measured permeation values is equal to the factor "m".

3. The method of claim 1, wherein the first closed container is a material package of first predetermined surface area, having a closure member formed thereon; and the second closed container is a material package of second predetermined surface area, a factor "m" times the surface area of the first closed container.

4. A method of measuring the permeation of vapors through the walls of tubing having a length $Z_1$, and having closure members at respective tubing ends, to obtain the measured permeation value $P_{t1}$ which is equal to the sum of the actual permeation value $X_{p1}$ representative of permeation through said tubing walls, plus the apparent permeation value $a_p$ representative of permeation through said closure members, comprising the steps of:

a) changing the length of said tubing to a length $Z_2$, wherein, to form a second tubing length $Z_2=mZ_1$, and applying the same closure members to the second tubing length;

b) measuring the permeation of vapors through the walls of said second tubing length, to obtain the measured permeation value $P_{t2}$ which is equal to the sum of the actual permeation value $X_{p2}$ representative of permeation through said tubing walls, plus the apparent permeation value $a_p$ representative of permeation through said closure members; and c) calculating the actual permeation value $X_{p1}$ by the equation $X_{p1}=P_{t1}-(P_{t2}-mP_{t1})/(1-m)$.

5. The method of claim 4, further comprising the steps of forming the ratio $P_{t2}/P_{t1}$ to obtain a ratio value, and comparing said ratio value with the value "m" to determine whether the ration value is equal to, or very nearly equal to, the value "m", thereby to validate said permeation measurements.

* * * * *